(12) United States Patent
Norman

(10) Patent No.: US 9,668,952 B2
(45) Date of Patent: Jun. 6, 2017

(54) SUNSCREEN FORMULATIONS

(75) Inventor: Greg Norman, Bedford, TX (US)

(73) Assignee: Mary Kay Inc., Addison, TX (US)

( * ) Notice: Subject to any disclaimer, the term of this patent is extended or adjusted under 35 U.S.C. 154(b) by 684 days.

(21) Appl. No.: 13/491,357

(22) Filed: Jun. 7, 2012

(65) Prior Publication Data

US 2013/0004443 A1    Jan. 3, 2013

Related U.S. Application Data

(60) Provisional application No. 61/494,682, filed on Jun. 8, 2011.

(51) Int. Cl.

| | | |
|---|---|---|
| *A61K 8/37* | (2006.01) | |
| *A61K 8/35* | (2006.01) | |
| *A61Q 17/04* | (2006.01) | |
| *A61K 8/40* | (2006.01) | |
| *A61K 8/86* | (2006.01) | |

(52) U.S. Cl.
CPC .................. *A61K 8/35* (2013.01); *A61K 8/37* (2013.01); *A61K 8/375* (2013.01); *A61K 8/40* (2013.01); *A61K 8/86* (2013.01); *A61Q 17/04* (2013.01); *A61K 2800/49* (2013.01); *A61K 2800/5922* (2013.01)

(58) Field of Classification Search
CPC .... A61K 8/37; A61K 8/35; A61K 2800/5922; A61K 8/40; A61Q 17/04
USPC ..................................................... 424/60, 59
See application file for complete search history.

(56) References Cited

U.S. PATENT DOCUMENTS

| | | | |
|---|---|---|---|
| 4,791,097 A * | 12/1988 | Walele et al. | 516/133 |
| 5,776,439 A | 7/1998 | Raspanti et al. | 424/59 |
| 5,783,173 A | 7/1998 | Bonda et al. | 424/59 |
| 6,787,147 B1 * | 9/2004 | Huner et al. | 424/401 |
| 7,135,165 B2 * | 11/2006 | Zofchak et al. | 424/59 |
| 2003/0180230 A1 | 9/2003 | Candau | 424/59 |
| 2004/0096404 A1 | 5/2004 | Zofchak et al. | 424/59 |
| 2005/0013781 A1 | 1/2005 | Dueva-Koganov et al. | 424/59 |
| 2007/0297996 A1 * | 12/2007 | Tanner | 424/59 |

FOREIGN PATENT DOCUMENTS

| | | |
|---|---|---|
| CN | 1050500 | 4/1991 |
| CN | 1424018 | 6/2003 |

OTHER PUBLICATIONS

Glogau R; "Seminars in Cutaneous Medicine and Surgery", vol. 15, (3), pp. 134-138, published Sep. 1996 by Elsevier.*
International Search Report and Written Opinion issued in PCT Application No. PCT/US2012/041366, dated Jan. 30, 2013.
Office Action and Search Report issued in Chinese Patent Application No. 201280033580.3, issued on Sep. 22, 2014.

* cited by examiner

*Primary Examiner* — Yanzhi Zhang
(74) *Attorney, Agent, or Firm* — Norton Rose Fulbright US LLP

(57) ABSTRACT

Disclosed are stable sunscreen compositions and corresponding methods for their use that are effective in protecting skin from UVA and UVB radiation. The composition uses a combination of ingredients to effectively and stably solubilize sunscreen agents to create a stable formulation.

14 Claims, No Drawings

SUNSCREEN FORMULATIONS

CROSS REFERENCE TO RELATED APPLICATIONS

This application claims the benefit of U.S. Provisional Application No. 61/494,682, filed Jun. 8, 2011, the contents of which are incorporated into the present application by reference.

BACKGROUND OF THE INVENTION

A. Field of the Invention

The present invention relates generally to sunscreen compositions.

B. Description of Related Art

Sunscreen compositions are known in the art. A problem with a majority of these compositions is that the sunscreen agents that absorb ultraviolet A (UVA) radiation between 400 to 315 nanometers are unstable and are not fully absorbed within the compositions. This results in compositions that are ineffective at protecting skin from UVA radiation, which is capable of causing damage to collagen fibers in the skin. Damage to collagen fibers, in turn, can lead to the appearance of fine lines and wrinkles and loss of elasticity in skin.

SUMMARY OF THE INVENTION

The present invention provides a solution to the current problems facing the use of UVA absorbing sunscreen agents by providing a combination of ingredients that effectively stabilizes and solublizes such agents within a given topical sunscreen composition. This results in a sunscreen composition that is effective in blocking both ultraviolet A (UVA) and ultraviolet B (UVB) radiation (i.e., radiation between 400 to 315 nm (UVA) and 315 to 280 nanometers (UVB)). UVB radiation burns skin. The end result is a stable and effective sunscreen that provides a user with broadband protection from UVA and UVB radiation, thereby reducing collagen damage while also preventing skin from being burned. In certain instances, the sunscreen composition can have an Sun Protection Factor (SPF) of at least about 30, 35, 40, 45, or 50 and a Protection Factor in UVA (PFA) of at least about 2, 4, 6, or 8. In particular, instances, the ratio of Sun Protection Factor (SPF) to PFA values is between about 4:1 to about 2:1, and more particularly about 3:1.

The inventor's solution resides in a combination of sunscreen ingredients, stabilization agents, and solubilizers. The compositions are such that the ultraviolet light absorbing agents remain stable (i.e., maintains ability to protect skin from UVA and UVB radiation and maintains SPF) and solubilized (i.e. no clumping or crystallization of sunscreen agents) within the composition when stored at room temperature (approximately 20-25° C.) for at least 1, 2, 3, 4, 5, 6, 7, 8, 9, 10, 11, or 12 months.

In one instance, for example, there is disclosed compositions having 3,3,5-trimethylcyclohexyl 2-hydroxybenzoate, 2-ethylhexyl 2-hydroxybenzoate, 2-Hydroxy-4-methoxyphenyl)-phenylmethanone, 1-(4-Methoxyphenyl)-3-(4-tert-butylphenyl)propane-1,3-dione, 2-ethylhexyl 2-cyano-3,3-diphenyl-2-propenoate, C12-15 alkyl benzoate, dipropylene glycol dibenzoate, and PPG-15 stearyl ether benzoate. The combination can also include dicaprylyl carbonate and/or ethylhexyl methoxycrylene. In a particular aspect, it was discovered that the following combination in the stated amounts was capable of producing a stable composition having an SPF of 35 and capable of blocking both UVA and UVB radiation: 10% by weigh of the composition (w/w) of 3,3,5-trimethylcyclohexyl 2-hydroxybenzoate; 5% w/w of 2-ethylhexyl 2-hydroxybenzoate; 4% w/w of 2-Hydroxy-4-methoxyphenyl)-phenylmethanone; 2% w/w of 1-(4-Methoxyphenyl)-3-(4-tert-butylphenyl)propane-1,3-dione; 2% w/w of 2-ethylhexyl 2-cyano-3,3-diphenyl-2-propenoate; 2.1% w/w of composition of C12-15 alkyl benzoate; 2% w/w of composition of dicaprylyl carbonate; 0.75% w/w of dipropylene glycol dibenzoate; and 0.15% w/w of PPG-15 stearyl ether benzoate. The composition can include 40% to 60% by weight of the composition of water. In particular aspects, it includes approximately 45 to 55% by weight of water. The remaining ingredients in the composition were base components that created a lotion. These ingredients can include 3 to 7% dimethicone, 1 to 3% w/w of butylenes glycol, 1 to 3% w/w of styrene/acrylates copolymer, 1 to 3% w/w of glycerin, 1 to 3% w/w of ceteareth-25, 1 to 3% w/w of dimethicone crosspolymer, and 1 to 3% w/w of magnesium aluminum silicate.

In another aspect, it was discovered that the following combination in the stated amounts was capable of producing a stable composition having any SPF of 50: 10% w/w of 3,3,5-trimethylcyclohexyl 2-hydroxybenzoate; 5% w/w of 2-ethylhexyl 2-hydroxybenzoate; 5% w/w of 2-Hydroxy-4-methoxyphenyl)-phenylmethanone; 5% w/w of 2-ethylhexyl 2-cyano-3,3-diphenyl-2-propenoate; 3% w/w of 1-(4-Methoxyphenyl)-3-(4-tert-butylphenyl)propane-1,3-dione; 1.4% w/w of C12-15 alkyl benzoate; 1% w/w of ethylhexyl methoxycrylene; 0.5% w/w of dipropylene glycol dibenzoate; and 0.1% w/w of PPG-15 stearyl ether benzoate. The composition can include 40% to 60% by weight of the composition of water. In particular aspects it includes approximately 40 to 50% by weight of water. The remaining ingredients in the composition were base components that created a lotion. These ingredients can include 3 to 5% w/w styrene/acrylates copolymer, 2 to 4% w/w of butylene glycol, 1 to 3% w/w of phenethyl benzoate, 1 to 3% w/w of butyloctyl salicylate, 1 to 3% w/w of silica, 1 to 3% w/w of methyl trimethicone, 1 to 3% w/w of glyceryl stearate, and 1 to 3% w/w of acrylates/dimethicone copolymer.

The compositions of the present invention can also include any combination of, or all of the following additional ingredients: a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In a further aspect, the aforementioned compositions did not include any additional ingredients sunscreen agents. Therefore, the compositions of the present invention, in certain aspects, do include or do not include additional sunscreen agents such as zinc oxide, titanium dioxide, camphor-based ingredients, triazine-based ingredients, PABA based ingredients, etc. In particular aspects, the compositions of the present invention do include or do not include para-aminobenzoic acid (PABA); PABA esters (glyceryl PABA, amyldimethyl PABA and octyldimethyl PABA); butyl PABA, ethyl PABA; ethyl dihydroxypropyl PABA; benzophenones such as sulisobenzone, and benzophenone-1,2, and 4-12); cinnamates such as isoamyl p-methoxycinnamate, cinoxate, diisopropyl methyl cinnamate, DEA-methoxycinnamate, ethyl diisopropylcinnamate, glyceryl octanoate dimethoxycinnamate and ethyl methoxycinnamate); cinnamate esters; salicylates such as benzyl salicylate, glycol salicylate, isopropylbenzyl, and salicylate; anthranilates; ethyl urocanate; octyl triazone; digalloy trioleate; glyceryl aminobenzoate; lawsone with dihydroxyacetone; ethylhexyl triazone; dioctyl butamido triazone; benzylidene malonate polysiloxane; terephthalylidene dicamphor sulfonic acid; disodium phenyl dibenzimidazole tetrasulfonate; diethylamino hydroxybenzoyl hexyl benzoate; bis diethylamino hydroxybenzoyl benzoate; bis benzoxazoylphenyl ethylhexylimino triazine; drometrizole trisiloxane; methylene bis-benzotriazolyl tetramethylbutyiphenol; bis-ethylhexyloxyphenol methoxyphenyltriazine; 4-methylbenzylidenecamphor; isopentyl 4-methoxycinnamate; kaolin; talc; petrolatum; and metal oxides (e.g., titanium dioxide and zinc oxide).

The compositions of the present invention can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14.

Also disclosed is a method of protecting skin from UVA and/or UVB radiation comprising topically applying any one of the compositions disclosed in this specification to skin, wherein topical application of the composition protects the skin from UVA and/or UVB radiation. In yet another embodiment there is disclosed a method of preventing erythemic skin or sunburned skin or aged skin (e.g., appearance of fine lines, wrinkles, aged spots, brown spots, etc.) comprising topically applying any one of the compositions disclosed in this specification to skin, wherein topical application of the composition prevents erythemic skin or sunburned skin or aged skin (e.g., appearance of fine lines, wrinkles, aged spots, brown spots, etc.).

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Dermatologically" or "pharmaceutically elegant" describes a composition that has particular tactile properties which feel pleasant on the skin (e.g., compositions that are not too watery or greasy, compositions that have a silky texture, compositions that are non-tacky or sticky, etc.). Dermatologically or pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

It is important to be able to protect skin from both UVA and UVB radiation. Over exposure to UVA radiation can lead to premature skin aging (e.g., increased appearance in fine lines and wrinkles, loss of skin elasticity, loss of skin moisture), symptoms that can take years to show on skin. By comparison, over exposure to UVB radiation, which can cause skin cancer, is commonly associated with sun tanned skin and sunburns. Because the symptoms of over exposure to UVB radiation can manifest within a short period of time (e.g., within minutes to hours of exposure), several sunscreen products protect against UVB radiation with limited protection offered against UVA radiation.

In this regard, a sunscreen product claiming to have a particular Sun Protection Factor ("SPF") number refers to the product's ability to protect the skin from sunburns. For instance, the SPF of a sunscreen is the amount of UV radiation required to cause a sunburn on the skin with the sunscreen on the skin, relative to the amount required to burn the skin without being protected with sunscreen. Applying a sunscreen having an SPF of 10 to skin provides the skin with 10 times the amount of protection from sunburns—i.e., it should take 10 times as long to obtain a sunburn when compared with unprotected skin.

One of the problems associated with SPF values is that this value only accounts for a product's ability to protect the skin against sunburns (which is caused by UVB radiation). An SPF value of a given product is not indicative of whether the product can protect skin from UVA radiation.

In contrast to SPF values, the Protection Grade of UVA ("PFA") value typically refers to a composition's ability to provide protection from UVA radiation. PFA values between 2-4 (also referred to as PA+) indicate that the composition provides limited protection against UVA radiation. PFA values between 4-8 (also referred to as PA++) indicate that the composition provides moderate protection from UVA radiation. PFA values of 8 or more (also referred to as PA+++) indicate that the composition provides a substantial protection from UVA radiation.

The inventor discovered that a combination of ingredients can be used to produce a sunscreen composition that is effective in blocking both UVA and UVB radiation, wherein the PA value is PA+++ and wherein the ratio of UVB protection to UVA protection is 3:1 or better (e.g., a 3:1 ratio means that for a product having SPF 35, the UVA protection (or PFA value) offered would be approximately 12). The end result is a stable and effective sunscreen that provides a user with broadband protection from UVA and UVB radiation, thereby reducing collagen damage while also preventing skin from being burned. In particular, the solution resides in a combination of sunscreen ingredients, stabilization agents, and solubilizers.

These and other non-limiting aspects of the present invention are provided in the following sections.

A. Sunscreen Agents

The sunscreen agents used in the compositions of the present invention include 3,3,5-trimethylcyclohexyl 2-hydroxybenzoate, 2-ethylhexyl 2-hydroxybenzoate, 2-Hydroxy-4-methoxyphenyl)-phenylmethanone, 1-(4-Methoxyphenyl)-3-(4-tert-butylphenyl)propane-1,3-dione, and 2-ethylhexyl 2-cyano-3,3-diphenyl-2-propenoate.

3,3,5-trimethylcyclohexyl 2-hydroxybenzoate is capable of absorbing UVA and UVB radiation. It is commercially available from a wide range of sources (see International Cosmetic Ingredient Dictionary and Handbook, 12$^{th}$ Edition, Volume 1, pages 1165-66, which is incorporated by reference). It has the following chemical structure:

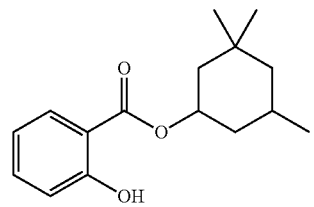

2-ethylhexyl 2-hydroxybenzoate is capable of absorbing UVB radiation. It is commercially available from a wide range of sources (see International Cosmetic Ingredient Dictionary and Handbook, 12$^{th}$ Edition, Volume 1, pages 966-67, which is incorporated by reference). It has the following chemical structure:

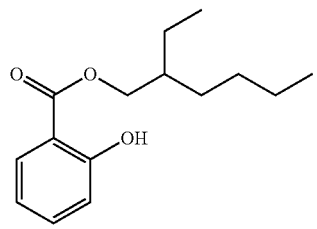

2-Hydroxy-4-methoxyphenyl)-phenylmethanone is capable of absorbing UVA and UVB radiation. It is commercially available from a wide range of sources (see International Cosmetic Ingredient Dictionary and Handbook, 12$^{th}$ Edition, Volume 1, pages 266-67, which is incorporated by reference). It has the following chemical structure:

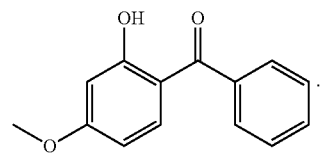 [SMILES: COc1ccc(C(=O)c2ccccc2)c(O)c1]

1-(4-Methoxyphenyl)-3-(4-tert-butylphenyl)propane-1,3-dione is capable of absorbing UVA radiation. It is commercially available from a wide range of sources (see International Cosmetic Ingredient Dictionary and Handbook, 12$^{th}$ Edition, Volume 1, page 359, which is incorporated by reference). It has the following chemical structure:

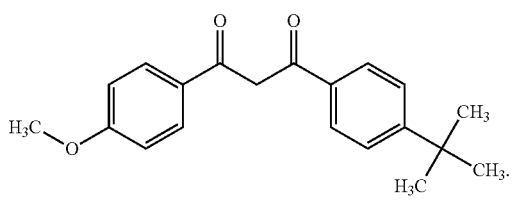 [SMILES: COc1ccc(C(=O)CC(=O)c2ccc(C(C)(C)C)cc2)cc1]

2-ethylhexyl 2-cyano-3,3-diphenyl-2-propenoate is capable of absorbing UVA and UVB radiation. It is commercially available from a wide range of sources (see International Cosmetic Ingredient Dictionary and Handbook, 12$^{th}$ Edition, Volume 2, pages 1683-84, which is incorporated by reference). It has the following chemical structure:

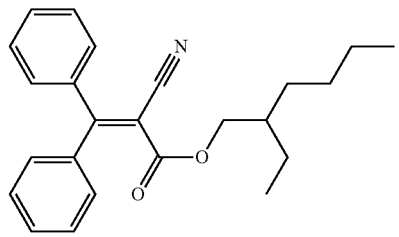

In addition to the above sunscreen agents, other can also be used but do not have to be used to obtain the results of the present invention. Therefore, the compositions of the present invention can include or can exclude any one of the following additional agents: para-aminobenzoic acid (PABA); PABA esters (glyceryl PABA, amyldimethyl PABA and octyldimethyl PABA); butyl PABA, ethyl PABA; ethyl dihydroxypropyl PABA; benzophenones such as sulisobenzone, and benzophenone-1,2, and 4-12); cinnamates such as isoamyl p-methoxycinnamate, cinoxate, diisopropyl methyl cinnamate, DEA-methoxycinnamate, ethyl diisopropylcinnamate, glyceryl octanoate dimethoxycinnamate and ethyl methoxycinnamate); cinnamate esters; salicylates such as benzyl salicylate, glycol salicylate, isopropylbenzyl, and salicylate; anthranilates; ethyl urocanate; octyl triazone; digalloy trioleate; glyceryl aminobenzoate; lawsone with dihydroxyacetone; ethylhexyl triazone; dioctyl butamido triazone; benzylidene malonate polysiloxane; terephthalylidene dicamphor sulfonic acid; disodium phenyl dibenzimidazole tetrasulfonate; diethylamino hydroxybenzoyl hexyl benzoate; bis diethylamino hydroxybenzoyl benzoate; bis benzoxazoylphenyl ethylhexylimino triazine; drometrizole trisiloxane; methylene bis-benzotriazolyl tetramethylbutyiphenol; bis-ethylhexyloxyphenol methoxyphenyltriazine; 4-methylbenzylidenecamphor; isopentyl 4-methoxycinnamate; kaolin; talc; petrolatum; and metal oxides (e.g., titanium dioxide and zinc oxide).

The compositions can have an sun protection factor (SPF) of 2, 3, 4, 5, 6, 7, 8, 9, 10, 11, 12, 13, 14, 15, 20, 25, 30, 35, 40, 45, 50, 55, 60, 70, 80, 90 or more, or any integer or derivative therein.

B. Solvents and Stabilizers

The ingredients used to solubilize and stabilize the sunscreen agents in the compositions of the present invention include C12-15 alkyl benzoate, dipropylene glycol dibenzoate, PPG-15 stearyl ether benzoate, dicaprylyl carbonate, and ethylhexyl methoxycrylene.

C12-15 alkyl benzoate is the ester of benzoic acid and C12-15 alcohols. It is commercially available from a wide range of sources (see International Cosmetic Ingredient Dictionary and Handbook, 12$^{th}$ Edition, Volume 1, pages 393-94, which is incorporated by reference). It has the following chemical structure:

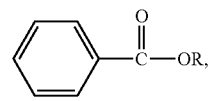

where R is the C12-15 alkyl group.

Dipropylene glycol dibenzoate is the diester of polypropylene glycol and benzoic acid. It is commercially available from a wide range of sources (see International Cosmetic Ingredient Dictionary and Handbook, 12$^{th}$ Edition, Volume 1, page 861, which is incorporated by reference).

PPG-15 stearyl ether benzoate is the ester of PPG-15 stearyl ether and benzoic acid. It is commercially available from a wide range of sources (see International Cosmetic Ingredient Dictionary and Handbook, 12$^{th}$ Edition, Volume 2, page 2235, which is incorporated by reference).

Dicaprylyl carbonate is the diester of carbonic acid and caprylyl alcohol. It is commercially available from a wide range of sources (see International Cosmetic Ingredient Dictionary and Handbook, 12$^{th}$ Edition, Volume 1, pages 771-72, which is incorporated by reference).

Ethylhexyl methoxycrylene is commercially available from HallStar (Chicago, Ill.) under the trade name SolaStay®. It has the following chemical structure:

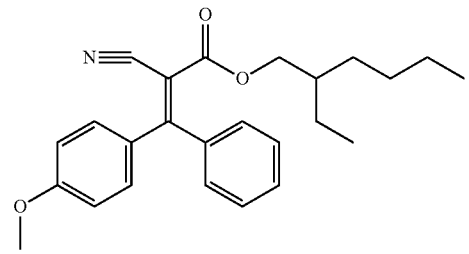

C. Compositions of the Present Invention

1. Combination and Amounts of Ingredients

It is contemplated that the compositions of the present invention can include 3,3,5-trimethylcyclohexyl 2-hydroxybenzoate, 2-ethylhexyl 2-hydroxybenzoate, 2-Hydroxy-4-methoxyphenyl)-phenylmethanone, 1-(4-Methoxyphenyl)-3-(4-tert-butylphenyl)propane-1,3-dione, 2-ethylhexyl 2-cyano-3,3-diphenyl-2-propenoate, C12-15 alkyl benzoate, dipropylene glycol dibenzoate, PPG-15 stearyl ether benzoate, dicaprylyl carbonate and/or ethylhexyl methoxycrylene. The compositions can also include additional ingredients described throughout this specification. The concentrations of these pulps and/or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of the ingredients identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the sunscreen agents, solubilizers, stabilizers, and additional ingredients can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. No. 6,387,398; U.S. Pat. No. 6,203,802; U.S. Pat. No. 5,411,744; Kreuter 1988).

3. Products

The compositions of the present invention can be incorporated into products. Non-limiting examples of products include cosmetic and pharmaceutical products. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), 12$^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, cross-linked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (prunus armeniaca) kernel oil, arginine, arginine aspartate, arnica montana extract, ascorbic acid, ascorbyl palmitate, aspartic acid, avocado (persea gratissima) oil, barium sulfate, barrier sphingolipids, butyl alcohol, beeswax, behenyl alcohol, beta-sitosterol, BHT, birch (betula alba) bark extract, borage (borago officinalis) extract, 2-bromo-2-nitropropane-1,3-diol, butcherbroom (ruscus aculeatus) extract, butylene glycol, calendula officinalis extract, calendula officinalis oil, candelilla (euphorbia cerifera) wax, canola oil, caprylic/capric triglyceride, cardamon (elettaria cardamomum) oil, carnauba (copernicia cerifera) wax, carrageenan (chondrus crispus), carrot (daucus carota sativa) oil, castor (ricinus communis) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (anthemis nobilis) oil, cholesterol, cholesterol esters, cholesteryl hydroxystearate, citric acid, clary (salvia sclarea) oil, cocoa (theobroma cacao) butter, coco-caprylate/caprate, coconut (cocos nucifera) oil, collagen, collagen amino acids, corn (zea mays) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (oenothera biennis) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (vitis vinifera) seed oil, hazel (corylus americana) nut oil, hazel (corylus avellana) nut oil, hexylene glycol, honey, hyaluronic acid, hybrid safflower (carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (jasminum officinale) oil, jojoba (buxus chinensis) oil, kelp, kukui (aleurites moluccana) nut oil, lactamide MEA, laneth-16, laneth-10 acetate, lanolin, lanolin acid, lanolin alcohol, lanolin oil, lanolin wax, lavender (lavandula angustifolia) oil, lecithin, lemon (citrus medica limonum) oil, linoleic acid, linolenic acid, macadamia ternifolia nut oil, magnesium stearate, magnesium sulfate, maltitol, matricaria (chamomilla recutita) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (olea europaea) oil, orange (citrus aurantium dulcis) oil, palm (elaeis guineensis) oil, palmitic acid, pantethine, panthenol, panthenyl ethyl ether, paraffin, PCA, peach (prunus persica) kernel oil, peanut (arachis hypogaea) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (mentha piperita) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (oryza sativa) bran oil, RNA, rosemary (rosmarinus officinalis) oil, rose oil, safflower (carthamus tinctorius) oil, sage (salvia officinalis) oil, salicylic acid, sandalwood (santalum album) oil, serine, serum protein, sesame (sesamum indicum) oil, shea butter (butyrospermum parkii), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (helianthus annuus) seed oil, sweet almond (prunus amygdalus dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (triticum vulgare) germ oil, and ylang ylang (cananga odorata) oil.

ii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanone, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol; tocophersolan, tocopheryl acetate, tocopheryl linoleate, tocopheryl nicotinate, tocopheryl succinate, and tris(nonylphenyl)phosphite.

iii. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

iv. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

v. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vi. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

vii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1 (Testing Vehicles)

Tables 1 and 2 describe generic skin testing formulations in which the sunscreen agents, solubilizers, and stabilizers can be incorporated into to determine the efficacy and stability of the composition to protect skin from UVA and UVB protection.

TABLE 1*

| Ingredient | % Concentration (by weight) |
|---|---|
| Phase A | |
| Water | q.s. |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Actives | as needed |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The actives to test include a combination of 3,3,5-trimethylcyclohexyl 2-hydroxybenzoate, 2-ethylhexyl 2-hydroxybenzoate, 2-Hydroxy-4-methoxyphenyl)-phenylmethanone, 1-(4-Methoxyphenyl)-3-(4-tert-butylphenyl)propane-1,3-dione, 2-ethylhexyl 2-cyano-3,3-diphenyl-2-propenoate, C12-15 alkyl benzoate, dipropylene glycol dibenzoate, PPG-15 stearyl ether benzoate, in combination with dicapryl carbonate or ethylhexyl methoxycrylene. The amounts of each of the ingredients can be varied to determine an optimal concentration for each ingredient.

TABLE 2*

| Ingredient | % Concentration (by weight) |
|---|---|
| Phase A | |
| Water | q.s. |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C** | |
| Actives | as needed |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The actives to test include a combination of 3,3,5-trimethylcyclohexyl 2-hydroxybenzoate, 2-ethylhexyl 2-hydroxybenzoate, 2-Hydroxy-4-methoxyphenyl)-phenylmethanone, 1-(4-Methoxyphenyl)-3-(4-tert-butylphenyl)propane-1,3-dione, 2-ethylhexyl 2-cyano-3,3-diphenyl-2-propenoate, C12-15 alkyl benzoate, dipropylene glycol dibenzoate, PPG-15 stearyl ether benzoate, in combination with dicapryl carbonate or ethylhexyl methoxycrylene. The amounts of each of the ingredients can be varied to determine an optimal concentration for each ingredient.

The inventor discovered that the following combination in the stated amounts resulted in a stable and effective sunscreen that has both UVA and UVB protection capabilities: 10% by weigh of the composition (w/w) of 3,3,5-trimethylcyclohexyl 2-hydroxybenzoate; 5% w/w of 2-ethylhexyl 2-hydroxybenzoate; 4% w/w of 2-Hydroxy-4-methoxyphenyl)-phenylmethanone; 2% w/w of 1-(4-Methoxyphenyl)-3-(4-tert-butylphenyl)propane-1,3-dione; 2% w/w of 2-ethylhexyl 2-cyano-3,3-diphenyl-2-propenoate; 2.1% w/w of composition of C12-15 alkyl benzoate; 2% w/w of composition of dicaprylyl carbonate; 0.75% w/w of dipropylene glycol dibenzoate; and 0.15% w/w of PPG-15 stearyl ether benzoate.

The inventor also discovered that the following combination in the stated amounts resulted in a stable and effective sunscreen that has both UVA and UVB protection capabilities: 10% w/w of 3,3,5-trimethylcyclohexyl 2-hydroxybenzoate; 5% w/w of 2-ethylhexyl 2-hydroxybenzoate; 5% w/w of 2-Hydroxy-4-methoxyphenyl)-phenylmethanone; 5% w/w of 2-ethylhexyl 2-cyano-3,3-diphenyl-2-propenoate; 3% w/w of 1-(4-Methoxyphenyl)-3-(4-tert-butylphenyl)propane-1,3-dione; 1.4% w/w of C12-15 alkyl benzoate, 1% w/w of ethylhexyl methoxycrylene; 0.5% w/w of dipropylene glycol dibenzoate; and 0.1% w/w of PPG-15 stearyl ether benzoate.

Example 2 (Sample Formulations)

The compositions in Tables 3 and 4 are sample formulations that were found to be particularly effective in providing broadband protection of UVA and UVB radiation. For instance, the Table 3 formulation was determined to have an SPF value of around 35 and also a PVA value of at least 8, thereby categorizing it as a PA+++ sunscreen. Indeed, this formulation falls into the 3:1 ratio protection of UVB to UVA. As for the Table 4 formulation, it was found to have an SPF of around 50 and also a PVA value of at least 8, thereby categorizing it as a PA+++ sunscreen. Further testing confirmed that the Tables 3-4 formulations are lotions that have long-term stability (i.e., the solubility of the sunscreen agents within the composition can be stored at room temperature/about 20-25° C. for 1 year) as determined by a standard heat stability test.

TABLE 3*

| Ingredient | % Concentration (by weight) |
|---|---|
| Water | 51.5 |
| 3,3,5-trimethylcyclohexyl 2-hydroxybenzoate | 10 |
| 2-ethylhexyl 2-hydroxybenzoate | 5 |
| 2-Hydroxy-4-methoxyphenyl)-phenylmethanone | 4 |
| C12-15 Alkyl Benzoate | 2.1 |
| 1-(4-Methoxyphenyl)-3-(4-tert-butylphenyl)propane-1,3-dione | 2. |
| Dicapryl Carbonate | 2 |
| 2-ethylhexyl 2-cyano-3,3-diphenyl-2-propenoate | 2 |
| Dipropylene Glycol Dibenzoate | 0.75 |
| PPG-15 Stearyl Ether Benzoate | 0.15 |
| Base** | q.s. |
| TOTAL | 100 |

*The composition was prepared by using standard mixing and heating steps.
**The base set of ingredients can be varied to create a desired composition (e.g., emulsion, solution, lotion, cream, etc.) having a desired viscosity. In this case, the primary set of base ingredients that were used included 5.9% dimethicone, 4% butylene glycol, 2.4% styrene/acrylates copolymer, 2% glycerin, 1.3% ceteareth-25, 1.1% dimethicone crosspolymer, 1% magnesium aluminum silicate, with the remaining ingredients being fillers, excipients, preservatives, and fragrances.

TABLE 4*

| Ingredient | % Concentration (by weight) |
|---|---|
| Water | 44 |
| 3,3,5-trimethylcyclohexyl 2-hydroxybenzoate | 10 |
| 2-ethylhexyl 2-hydroxybenzoate | 5 |
| 2-Hydroxy-4-methoxyphenyl)-phenylmethanone | 5 |
| 2-ethylhexyl 2-cyano-3,3-diphenyl-2-propenoate | 5 |
| 1-(4-Methoxyphenyl)-3-(4-tert-butyl-phenyl)propane-1,3-dione | 3 |

TABLE 4*-continued

| Ingredient | % Concentration (by weight) |
|---|---|
| C12-15 Alkyl Benzoate | 1.4 |
| Ethylhexyl Methoxycrylene | 1 |
| Dipropylene Glycol Dibenzoate | 0.5 |
| PPG-15 Stearyl Ether Benzoate | 0.1 |
| Base** | q.s. |
| TOTAL | 100 |

*The composition was prepared by using standard mixing and heating steps.
**The base set of ingredients can be varied to create a desired composition (e.g., emulsion, solution, lotion, cream, etc.) having a desired viscosity. In this case, the primary set of base ingredients that were used included 3.8% styrene/acrylates copolymer, 3% butylene glycol, 2% phenethyl benzoate, 2% butyloctyl salicylate, 4% silica, 2.4% methyl trimethicone, 1.1% glyceryl stearate, and 1.6% acrylates/dimethicone copolymer, with the remaining ingredients being fillers, excipients, preservatives, and fragrances.

Example 3 (Additional Assays)

Compositions of the present invention (e.g., those disclosed in Tables 1-4) can be assayed to determine the ability of such compositions to treat other skin-related conditions.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture Content. The outer layer of the skin has distinct electrical properties. When skin is dry it conducts electricity very poorly. As it becomes more hydrated increasing conductivity results. Consequently, changes in skin impedance (related to conductivity) can S be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Micro-texture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

All of the active ingredients, compositions, or methods disclosed and claimed in this specification can be made and executed without undue experimentation in light of the present disclosure. While the active ingredients, compositions, or methods of this invention have been described in terms of particular embodiments, it will be apparent to those of skill in the art that variations may be applied to the active ingredients, compositions, or methods and in the steps or in the sequence of steps of the method described herein without departing from the concept, spirit and scope of the invention.

The invention claimed is:

1. A sunscreen composition comprising:
   (i) a combination of ultraviolet light absorbing agents including:

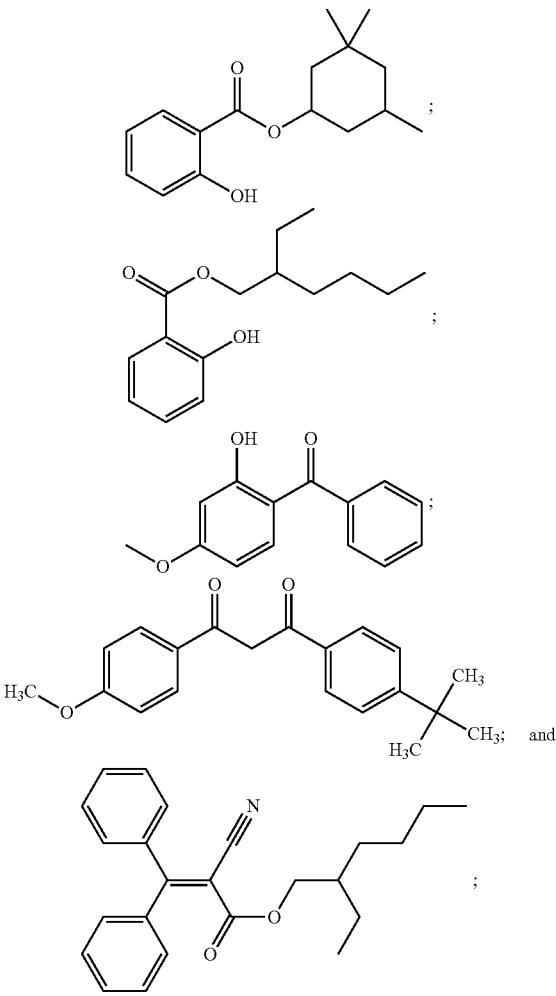

and (ii) a combination of solubilizers and stabilizers to solubilize and stabilize said ultraviolet light absorbing agents, said combination including $C_{12-15}$ alkyl benzoate, dipropylene glycol dibenzoate, Polypropylene Glycol-15 (PPG-15) stearyl ether benzoate, and dicaprylyl carbonate, wherein said ultraviolet light absorbing agents are stable and solubilized within the sunscreen composition when stored at room temperature for 1 month, and wherein the sunscreen has a Sun Protection Factor (SPF) of at least 35 and a Protection Factor in UVA (PFA) of at least 4.

2. The sunscreen composition of claim 1, wherein the ratio of SPF to PFA is between about 4:1 to about 2:1.

3. The sunscreen composition of claim 2, wherein the ratio of SPF to PFA is about 3:1.

4. The sunscreen composition of claim 1, wherein the composition includes:

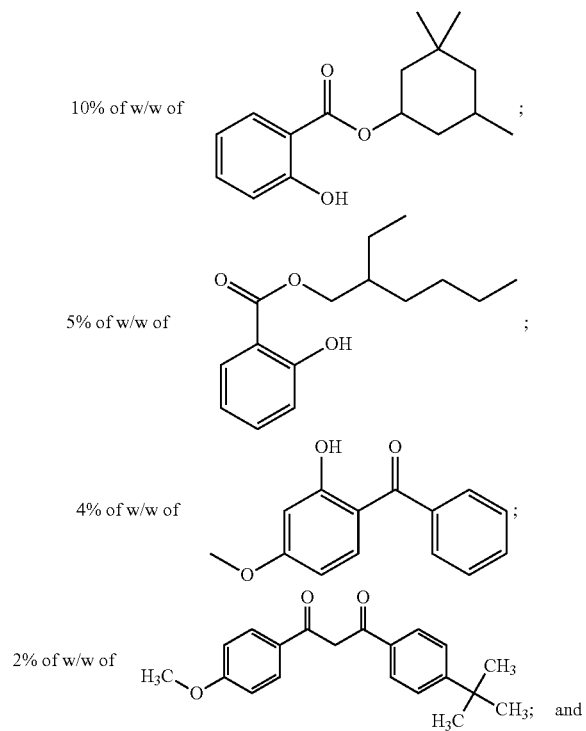

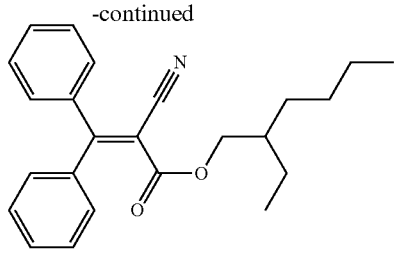

5. The sunscreen composition of claim 4, wherein the composition includes 2.1% w/w of $C_{12-15}$ alkyl benzoate, 2% w/w of dicaprylyl carbonate, 0.75% w/w of dipropylene glycol dibenzoate, and 0.15% w/w of PPG-15 stearyl ether benzoate.

6. The sunscreen composition of claim 5, wherein the composition further includes 45 to 55% by weight of water, 3 to 7% dimethicone, 1 to 3% w/w of butylene glycol, 1 to 3% w/w of styrene/acrylates copolymer, 1 to 3% w/w of glycerin, 1 to 3% w/w of ceteareth-25, 1 to 3% w/w of dimethicone crosspolymer, and 1 to 3% w/w of magnesium aluminum silicate.

7. The sunscreen composition of claim 6, wherein the composition is formulated as a cream, lotion, or serum.

8. The sunscreen composition of claim 7, wherein the composition does not include any additional ultraviolet light absorbing agents.

9. The sunscreen composition of claim 8, wherein the ratio of SPF to PFA is about 3:1.

10. The sunscreen composition of claim 1, wherein the composition has a SPF of about 35 and a Protection Grade of UVA (PA) rating of PA+++.

11. A method of protecting skin from ultraviolet A (UVA) and ultraviolet B (UVB) radiation comprising topically applying the composition of claim 1 to skin, wherein topical application of the composition protects the skin from UVA and UVB radiation.

12. A method of preventing or reducing the appearance of erythemic skin, sunburned skin, or aged skin comprising topically applying the compositions of claim 1 to skin, wherein topical application of the composition prevents or reduces the appearance of erythemic skin, sunburned skin, or aged skin.

13. The method of claim 12, wherein aged skin is skin having fine lines and wrinkles.

14. The sunscreen composition of claim 1, wherein the composition is an emulsion and comprises a surfactant.

* * * * *